(12) United States Patent
Raidel et al.

(10) Patent No.: US 8,541,644 B2
(45) Date of Patent: Sep. 24, 2013

(54) ABSORBENT BODY FOR AN ABSORBENT ARTICLE AND METHOD OF PRODUCING AN ABSORBENT BODY

(75) Inventors: Maria Raidel, Fuerth (DE); Franz Aschenbrenner, Kastl (DE); Jan Ullman, Nuremberg (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/480,645

(22) Filed: May 25, 2012

(65) Prior Publication Data

US 2012/0322639 A1 Dec. 20, 2012

Related U.S. Application Data

(63) Continuation of application No. 10/049,891, filed as application No. PCT/EP00/07836 on Aug. 11, 2000, now Pat. No. 8,187,242.

(30) Foreign Application Priority Data

Aug. 13, 1999 (DE) .................................. 199 38 437

(51) Int. Cl.
*A61F 13/15* (2006.01)
(52) U.S. Cl.
USPC ........................................................ 604/378
(58) Field of Classification Search
USPC ............. 604/385.01, 385.11, 385.22, 385.24, 604/385.27; 156/60, 62.6, 73.3, 73.4, 174, 156/250, 256, 265
See application file for complete search history.

(56) References Cited

U.S. PATENT DOCUMENTS

| | | | |
|---|---|---|---|
| 4,988,344 A | 1/1991 | Reising et al. |
| 5,387,210 A | 2/1995 | Murakami |
| 5,484,430 A | 1/1996 | Osborn, III |
| 5,807,365 A | 9/1998 | Luceri |
| 5,897,541 A | 4/1999 | Uitenbroek et al. |
| 5,925,026 A | 7/1999 | Arteman et al. |
| 6,050,984 A | 4/2000 | Fujioka et al. |

FOREIGN PATENT DOCUMENTS

| | | |
|---|---|---|
| DE | 196 40 451 A | 4/1998 |
| EP | 0 581 258 | 2/1994 |
| EP | 0 687 453 | 12/1995 |
| EP | 0 804 916 | 11/1997 |
| EP | 0 815 817 | 1/1998 |
| EP | 0 914 811 | 5/1999 |

*Primary Examiner* — Melanie Hand
(74) *Attorney, Agent, or Firm* — Armstrong Teasdale LLP

(57) ABSTRACT

A method of producing an absorbent body for an absorbent article having an absorbent body disposed generally centrally of the article and adapted for absorbing liquid body waste released by the wearer includes passing a first cut-out from a first web material through a nip, passing a second web material through the nip whereby the cut-out from the first web material overlays the second web material as the cut-out and the second web material pass through the nip, and performing one of the following as the cut-out from the first web material and the second material together pass through the nip: forming a fold line in the second web material at the peripheral edge of the cut-out of the first web material and forming a second cut-out from the second web material having substantially the same shape as the first cut-out from the first web material.

20 Claims, 10 Drawing Sheets

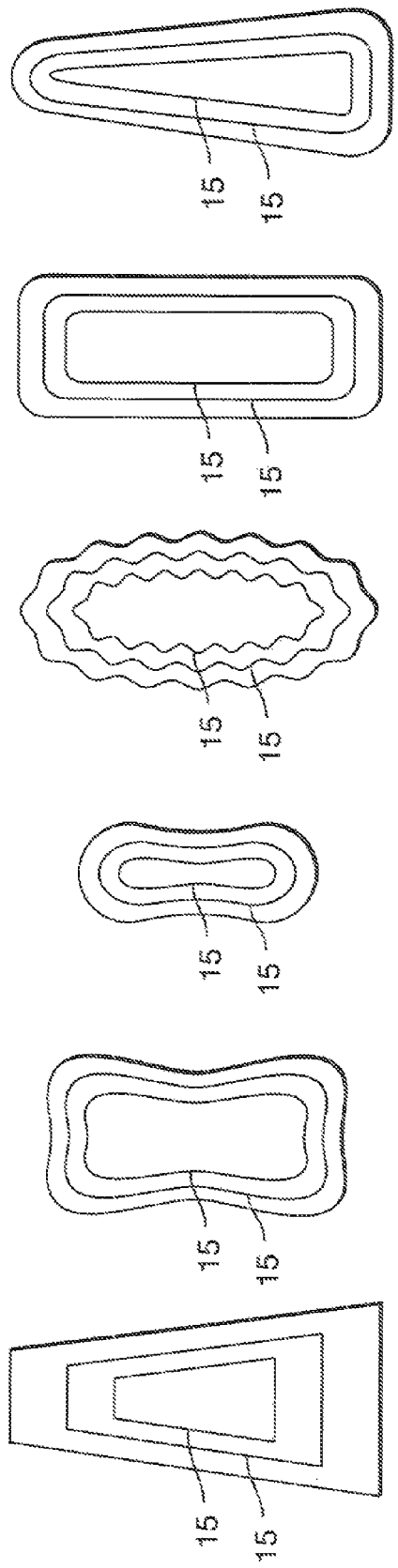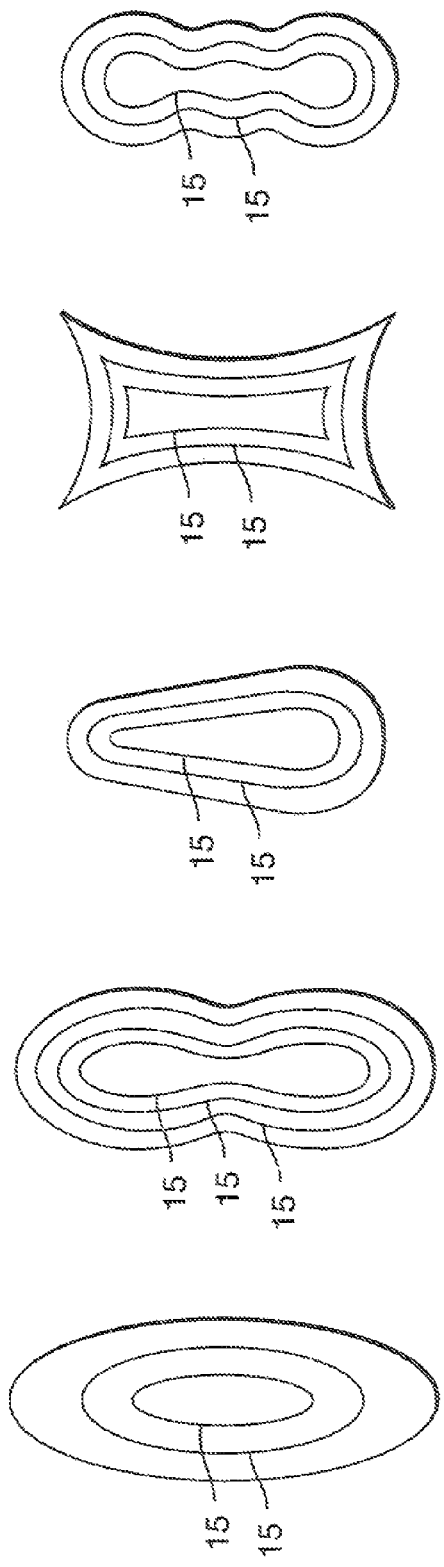

ABSORBENT BODY FOR AN ABSORBENT ARTICLE AND METHOD OF PRODUCING AN ABSORBENT BODY

This application is a continuation of application Ser. No. 10/049,891 filed on Aug. 11, 2000. The entirety of application Ser. No. 10/049,891 is hereby incorporated by reference.

BACKGROUND OF THE INVENTION

The present invention concerns an absorbent article comprising a segmented absorbent body and a method of producing an absorbent body, in particular a segmented absorbent body. The absorbent body is preferably arranged between a liquid-permeable cover layer and a liquid-impermeable backing layer.

It is known from the state of the art how to produce absorbent articles containing the absorbent bodies. As a rule, these absorbent bodies are arranged between a liquid-permeable cover layer and a liquid-impermeable backing layer. Such absorbent articles include, for example, menstrual hygiene napkins, disposable diapers, training diapers and incontinence articles for adults as well as similar articles. As a rule, the absorbent bodies of the traditional type contained in these absorbent articles contain pulped cellulose or sheeting materials of cellulose/synthetic fiber blends as the absorbent material.

These materials are supposed to serve to absorb body fluids such as menstrual fluid and retain them in a napkin. The menstrual fluid should preferably remain inside the absorbent article even under pressure and if possible it should not be detectable from the outside. The absorbent article and in particular the absorbent body in the absorbent article should prevent the secreted body fluids from soiling the wearer's body and/or spotting the adjacent items of clothing.

The sheeting materials used for the absorbent material are either arranged continuously (i.e., they cover the total length of the napkin or they form rectangular inserts, for example) or they may have cutouts. The cutouts are preferably arranged in a top layer of the absorbent material and should serve to convey the fluid away from the body of the wearer of the absorbent article as rapidly and efficiently as possible and to release it downward into the other absorbent and storing layers of the absorbent article.

There are several possibilities of storing the fluid delivered in the absorbent article. One of these possibilities is to convey the fluid secreted as rapidly and directly as possible to a lower area of the article which is preferably arranged directly above the liquid-impermeable backing layer, from whence the fluid is then distributed in the longitudinal direction. As soon as this bottom absorbent distributor layer becomes saturated with the fluid secreted, the absorbent layers closer to the wearer's body then become saturated with the fluid.

Another possibility is for the secreted body fluid to be distributed as rapidly as possible in the longitudinal directions of the napkin, from whence in the remaining course it then diffuses toward the side of the absorbent article facing away from the wearer's body.

Apart from providing a cutout in an upper area of the absorbent material in an absorbent article, there are various other possibilities for improving the distribution of fluid in an absorbent article. These possibilities involve, for example, providing various layers within the absorbent article to function as flow layers, storage layers, transfer layers or distributing layers. Such layers may be defined by different materials, for example. Another possibility is to provide embossed lines in a layer of the absorbent material in an absorbent article through which the fluid is guided in predetermined and preferred paths, thus preventing the area of the absorbent article exposed to the fluid from becoming saturated. Another possibility of preventing leakage and promoting penetration of the secreted fluid into the interior of the absorbent material is to provide elastic or elevated side areas (cuffs) which should prevent leakage at the sides.

SUMMARY OF THE INVENTION

With the absorbent articles described above, it is also important that the absorbent article is adapted to the shape of the wearer's body, preferably conforming to the shape of the wearer's body, so that the wearer is not hindered by the absorbent article. It is especially preferable for the absorbent article not to be perceived by the wearer at all. Furthermore, the absorbent article should be prevented from rubbing against the wearer's body in a manner that would be unpleasant for the wearer, even leading to red and irritated skin. There have been various proposals for achieving such an optimum suppleness and adaptability to the wearer's body. Many of these proposals concern the use of materials that are already rather supple anyway and therefore offer increased comfort for wear. However, such materials are often less suitable than an absorbent material for their actual function. A typical absorbent material such as coform will have a certain stiffness which can be reduced only by also surrendering certain advantageous absorbent properties.

Therefore, one object of the present invention is to provide an absorbent article that does not have the abovementioned disadvantages according to the state of the art. In particular, one object of the present invention is to provide an article that prevents in particular leakage of secreted fluid into the side areas of the absorbent article (side leakage) in an improved manner.

Another object of the present invention is to provide an absorbent article which permits especially good suppleness and individual adaptation to the wearer's body.

Finally, another object of the present invention is to reduce the stiffness of a continuous web of material in such a manner that it leads to an improved suppleness and better adaptation to the wearer's body.

The term "segmented" as used here is understood to refer to the subdivision of the absorbent body into subareas, i.e., segments, defined by at least one dividing seam or fold line.

The term "dividing seam" or "fold line" is understood to refer to the areas of a material processed for separation to form the segments of the absorbent body. That is, the dividing seam, or fold line, refers to creases, cuts or other indentations formed in the absorbent body to define segments of the absorbent body that are capable of folding relative to each other. The term "processed for separation" is thus understood here to refer to the separation methods, e.g., methods of creasing, punching, cutting, indenting, etc. known in the state of the art by means of which individual areas of a material layer can be separated, e.g., segmented, from one another. "Processing for separation" thus produces in general dividing seams, or fold lines, in these materials.

The dividing seam may consist of a continuous or interrupted dividing line. If the dividing seam is executed in the form of an interrupted dividing line, the different areas of material are still joined together by bridge areas. In addition, a dividing seam can be worked through the entire thickness of one or more layers of material or through only partial areas of the thickness or one or more layers of material. The latter is preferred if the layer of material is still to form a unit.

Providing an absorbent body which is segmented by at least one dividing seam in at least partial areas yields an absorbent article which achieves optimum suppleness and individual adaptation to the wearer's body. The segmentation, which forms intended breaking points, eliminates or reduces the stiffness of the absorbent material in an inventive manner, leading to improved suppleness. In addition, the dividing seams improve the rapid penetration of the secreted fluid into the depth of the absorbent body, thus preventing side leakage in an improved manner and thereby also preventing soiling of the wearer's body and/or clothing.

The dividing seams yield stable individual elements that emboss and compress the absorbent body. Thus, areas of different density are formed within each individual element. Density gradients are formed along the dividing seams, optimizing fluid transport. On the whole, the absorbent body is especially compressed in the area around the dividing seams. The fluids such as menstrual fluid to be absorbed by the absorbent body may consist of various components which have different properties and are transported to different extents through a uniformly structured absorbent body. Due to the presence of areas of different density and due to the density gradient prevailing along the dividing seams, it is possible for each fluid component to find an area especially suitable for its transport.

To further improve upon the side leakage protection, it is especially preferable to increase the number of dividing seams in the edge area of the absorbent body.

The segmentation of the absorbent body yields many small individual elements that are stabilized on all sides and are especially preferably applied to a flexible elastic substrate. Therefore, the segments are displaceable with respect to one another. Thus, the absorbent body can be adapted especially well to the body contours of the wearer.

In a preferred embodiment of this invention, the absorbent body has at least two layers, with at least one of the layers being segmented. This permits an optimum combination of the properties of the segmented layer with those of an unsegmented layer, for example.

Preferred shapes for the segments created by the dividing seams in the absorbent body may be squares and/or diamonds and/or circles as well as any other suitable geometric shape. In another especially preferred embodiment of this invention, the absorbent body is designed with at least two layers, where at least one layer of the absorbent body facing the wearer's body is smaller than at least one other layer of the absorbent body facing away from the wearer's body.

The layer of the absorbent body facing the wearer's body faces the wearer's body when the absorbent article is in use and is thus arranged over the layer of the absorbent body facing away from the wearer's body. The latter faces away from the wearer's body when the absorbent article is in use.

Providing an absorbent body which is designed with at least two layers yields various functions as follows, where at least one layer facing the wearer's body and at least one layer facing away from the wearer's body are formed, and at least one layer of the absorbent body facing the wearer's body is smaller than at least one other layer of the absorbent body facing away from the wearer's body, so that the entire absorbent material has a predetermined "intended breaking line":

providing an "intended breaking line" as defined above yields optimum suppleness and individual adaptation to the wearer's body, providing the two-layer absorbent body where the layer of the absorbent body facing the wearer's body is smaller than the layer of the absorbent body facing away from the wearer's body creates a liquid storage area in the center of the napkin to improve the side leakage protection, preferably the minimum of one layer of the absorbent body facing the wearer's body has less than 70% of the area of the minimum of one layer of the absorbent body facing away from the wearer's body; even more preferably, the minimum of one layer of the absorbent body facing the wearer's body has less than 50% of the area of the minimum of one layer of the absorbent body facing away from the wearer's body; even more preferably, the minimum of one layer of the absorbent body facing the wearer's body has less than 30% of the area of the minimum of one layer of the absorbent body facing away from the wearer's body.

The minimum of one layer of the absorbent body facing the wearer's body is formed by the shaping methods known in the state of the art. It is especially preferable for the minimum of one layer of the absorbent body facing the wearer's body to be punched out or cut out.

The term "layer" as used in the present invention includes layers of one or more materials as well as multilayer composites such as laminates.

In an especially preferred embodiment of the present invention, one or more layers arranged beneath and/or above the minimum of one layer of the absorbent body facing the wearer's body has been processed for separation and thus segmented along the same contours as the minimum of one layer of the absorbent body facing the wearer's body.

The shaping of the minimum of one layer facing the wearer's body can be performed here by one of the methods known in the state of the art, such as cutting off or out, molding, punching, etc. The layer of the absorbent body facing away from the wearer's body as well as the layers of the absorbent body above and/or below that are processed for separation, e.g., cut or punched.

In another especially preferred embodiment of the present invention, the minimum of one layer of the absorbent body facing the wearer's body and one or more of the layers arranged above and/or below that are processed for separation along the same contours as the minimum of one layer of the absorbent body facing the wearer's body.

According to an especially preferred embodiment of the present invention, not only the minimum of one layer of the absorbent body facing the wearer's body is punched out or cut out, but also additional layers which may be present in the napkin are also punched or cut out.

Apart from the minimum of one layer of the absorbent body facing the wearer's body, it is especially preferable for the layers of the absorbent body facing away from the wearer's body beneath that to be processed for separation. However, then preferably the "frame grid" of the minimum of one layer of the absorbent body facing the wearer's body remains in the napkin, while the "punched grid" of the minimum of one layer of the absorbent body facing the wearer's body is removed in any case. The term "frame grid" as used here is understood to refer to the part of a layer of material located outside a dividing seam provided in it, e.g., a punched or cut area, and forming a part of the absorbent article. In other words, the minimum of one layer of the absorbent body facing away from the wearer's body is segmented by separation processing into a frame grid and an area enclosed by the frame grid. The term "punched grid" here is understood to refer to the part of a layer of material located outside the dividing seam, e.g., the punched or cut area, and not forming part of the absorbent article. The "frame grid" of course has a preferred shape for the absorbent article, which in the present case preferably corresponds to the overall shape of the absorbent article. This yields the absorbent body according to this invention, comprising at least one layer facing the wearer's body which is smaller, due to removal of the "punched grid", than the minimum of one layer arranged at a distance from the body, likewise processed for separation, e.g., cut or punched, and where the "frame grid" forms a part of the absorbent article, however.

By providing an absorbent body having at least two layers, where the minimum of one layer of the absorbent body facing the wearer's body has a smaller area than the minimum of one layer of the absorbent body facing away from the wearer's body, and due to the fact that the layer of the absorbent body facing away from the wearer's body has been punched and/or cut in a manner corresponding to the punched or cut out area of the layer of the absorbent body facing the wearer's body, this provides an absorbent article which eliminates the stiffness of a continuous web of material due to the cutouts and/or punched areas, in addition to an optimum suppleness and an individual adaptation to the wearer's body and an improvement in side leakage. It is known that the preferred absorbent material used in absorbent articles has a certain stiffness. If an entire web of material of such an absorbent material is provided in an absorbent article, as is usually necessary to guarantee adequate absorption and storage properties of the absorbent article, this leads to a stiffness of the absorbent material which makes the absorbent article uncomfortable to wear on the whole.

This leads to a suboptimal suppleness, and adaptation to the individual wearer's body is not guaranteed. The stiffness of a continuous web of material can be eliminated in an inventive manner by the cutout/punched out areas in the minimum of one layer of the absorbent body facing away from the wearer's body. This leads to a great improvement in suppleness and the possibility of an individual adaptation to the body of the wearer.

Furthermore, the permeable areas of the cutout or punched out areas facilitate more rapid penetration of the secreted fluid deeper into the napkin and thus prevent side leakage in an improved manner and thus prevent soiling of the wearer's body or the adjacent clothing in the area of the absorbent article and thus contribute toward a reduction in surface moisture. This effect is increased by the altered capillarity of the materials in the immediate vicinity of the punched out/cutout areas. The material is compressed there, thus increasing the capillarity. This causes a more effective fluid transport into these areas which thus function as "intended penetration areas" where the fluid is transported especially rapidly and effectively.

Preferably the minimum of one layer of the absorbent body facing the wearer's body, which is smaller than the minimum of one layer of the absorbent body facing away from the wearer's body, is in the shape of an oval. Other possible shapes include a rectangular shape, a tongue shape, a triangular shape, a circular shape, a trapezoidal shape or an hourglass shape. Any other geometric shape is also conceivable for the present invention, as long as it meets the requirements specified above.

In another preferred embodiment of this invention, additional dividing seams, e.g., cut-out or punched-out areas, are provided in the minimum of one layer of the absorbent body facing the wearer's body and/or within one or more layers of the absorbent body arranged above and/or below that. These additional dividing seams, e.g., cut-out or punched-out areas, are arranged inside the areas of the above-mentioned layers determined by the shape of the minimum of one layer of the absorbent body facing the wearer's body. For example, the minimum of one layer of the absorbent body facing the wearer's body may have an oval shape and may have additional oval cut-out or punched-out areas concentric with the former. The additional layers of the absorbent body may also have these additional oval punched out areas arranged concentrically, where the corresponding punched areas in the different layers essentially coincide.

The additional dividing seams, e.g., cut-out or punched-out areas in the various layers of the absorbent body, improve the suppleness and adaptability to the body of the individual wearer through the resulting segmentation, while also improving the fluid transport within the absorbent article.

Preferably the absorbent article according to the present invention comprises the following components:
a) a liquid-permeable cover layer and
b) a liquid-impermeable backing layer,
where the absorbent body is arranged between the cover layer and the backing layer.

The minimum of one layer of the absorbent body facing away from the wearer's body preferably has elongated side areas. The cover layer and/or the backing layer may extend laterally outward from the elongated side parts of the absorbent body to provide a pair of elongated side edges for the absorbent article. The cover layer is arranged on the side facing the wearer's body and should be arranged next to the wearer during use. The backing layer is arranged parallel to the cover layer and should be next to the wearer's underwear garment when being used.

The cover layer may be manufactured from materials known in the state of the art. They should be liquid permeable. Known materials include, for example, card weaves and spunbonded nonwovens made of polyester, polypropylenes, polyethylene, nylon or other heat-bonded fibers. Other polyolefins such as copolymers of polypropylene and polyethylene, linear, low-density polyethylene fiber nonwovens which are finely perforated or mesh-like materials are also suitable. Other suitable materials include composite materials of polymers and a nonwoven material. The composite layers are usually formed by extrusion of a polymer on a layer of a spunbonded nonwoven to form an integral layer. This material is preferred, because the outer surface is not irritating to the skin of the wearer and it has a pleasant feel.

With regard to the above-mentioned cover layer, it is also advantageous that this cover layer has the following features. In general, a cover layer is provided to achieve the greatest possible comfort and great adaptability to the wearer's body and should divert fluid to the body under it. The cover layer may be constructed of a relatively nonabsorbent liquid-permeable material, where the cover layer may be constructed of any woven or nonwoven material through which body fluid which contacts its surface can flow easily. The cover layer is preferably made of a material that permits the passage of fluid without drawing the fluid horizontally in parallel to the cover layer to any great extent. In addition, the cover layer should retain little or no fluid in its structure, so that a relatively dry surface is provided next to the wearer's skin. In general, the cover layer is a single layer of a material with a width sufficient to cover the surface of the absorbent body facing the wearer's body. The cover layer preferably extends to the longitudinal edges and is bonded to the backing layer. The cover layer may be bonded to the backing layer using any known method which does not leave any hard or uncomfortable residues that would annoy the wearer. Those skilled in the art are familiar with methods of bonding the various materials and for bonding other possible materials in the absorbent article according to the present invention, including the use of pressure-sensitive adhesives, hot-melt adhesives, two-sided adhesive sheets, ultrasonic welding and heat sealing, to name but a few. Adhesives such as hot-melt adhesives may be used uniformly or in the form of a continuous or noncontinuous layer.

The cover layer may be designed in two parts. Two parts here means that the cover layer may consist of an outer area and a central area. The outer area is preferably essentially in the area of the longitudinal edges of the absorbent article and, if there are wings on the napkin, it may also be designed in the area of the wings, where the central area is designed in the remaining central area of the absorbent article. The two parts of the cover layer can be bonded together. Such a bond can be produced by using a hot-melt adhesive or by providing a welded seam. Other forms of bonds that are known in this field of the art are also included here.

If the cover layer is designed in two parts, the central area of the cover layer and/or the outer area of the cover layer may be a spunbonded nonwoven of polypropylene having an especially thick fiber and thus a high denier. Furthermore, this spunbonded nonwoven may contain more pigment, e.g., have a higher titanium dioxide content to improve the masking properties. Such a polypropylene spunbonded nonwoven with the properties described above may have, for example, a basis weight of 15 to 50 $g/m^2$ preferably 20 $g/m^2$. In a preferred embodiment, it is 70 mm wide.

Other possible materials for the outer area of the cover layer and/or the inner area of the cover layer include spunbonded nonwovens or carded nonwovens of polypropylene, for example, with a basis weight of 15 to 50 $g/m^2$, preferably 20 $g/m^2$. The preferred composition of the cover layer is a two-part cover layer, where the outer area of the cover layer is made of a polypropylene spunbonded nonwoven with a basis weight of 20 $g/m^2$, and where the inner area of the cover layer is made of a perforated polypropylene spunbonded nonwoven in a weight of 20 $g/m^2$. The two parts of the cover layer are preferably bonded by a welded seam.

The backing layer may be made of any desired material that is liquid-impermeable. The backing layer preferably allows atmospheric vapor and moisture to pass through the absorbent article while preventing body fluid from passing through. A suitable material is a microembossed polymer film such as polyethylene or polypropylene with an approximate thickness of 0.025 to 0.13 mm. Two-component films may also be used, as well as nonwoven materials or woven materials which are treated to make them liquid impermeable. Other suitable materials include films filled with $CaCO_3$ or polyolefin in foams. A polyethylene foam with a thickness in the range of approximately 0.5 mm to approximately 10 mm can be mentioned as an example.

The absorbent body in the absorbent article provides a means for absorbing the secreted fluid, in particular menstrual fluid. The total absorption capacity of the absorbent body should correspond to the anticipated loading in the course of the intended use of the absorbent article. In addition, the size and shape of the absorbent body may vary. As explained above, the absorbent body may have the various shapes mentioned above in the area of the minimum of one layer of the absorbent body facing the wearer's body. The minimum of one layer of the absorbent body facing away from the wearer's body may also have various shapes, but at any rate it should be larger than the minimum of one layer facing the wearer's body. It can function as a secondary reservoir. The layer of the absorbent body facing away from the wearer's body may be, for example, rectangular with rounded longitudinal edges, tongue-shaped or oval or it may have any other known geometric shape known in the related art.

The absorbent body is generally made of one or more materials which together are essentially hydrophilic, compressible, adaptable and non-irritating for the skin of the wearer. Suitable materials are well known in the field and include, for example, various natural or synthetic fibers, cellulose fibers, regenerated cellulose or cotton fibers or a blend of cellulose and other fibers, melt-blown polymers such as polyester and polypropylene. The absorbent layers may also include other well-known materials which are used with absorbent articles, including several layers of a cellulose filling, rayon fibers, cellulose sponge, hydrophilic synthetic sponges, such as polyurethane and the like.

In addition, especially when used in incontinence articles, the absorbent body may contain superabsorbers which are very effective in retaining body fluids. Superabsorbers have the ability to absorb a large amount of fluid in relation to their own weight. Typical superabsorbers used in absorbent articles such as sanitary napkins can absorb between approximately 5 and 60 times their weight in body fluids.

A preferred material for the absorbent layer is a coform material which contains, for example, cellulose and polypropylene in a weight ratio of 70:30 and has a basis weight of 150 $g/m^2$ and is used together with a polypropylene spunbonded nonwoven backing with a basis weight of 17 $g/m^2$. As an alternative, for example, a coform material containing cellulose and polypropylene in a weight ratio of 60:40 and having a basis weight of 90 $g/m^2$ may also be used together with a polypropylene spunbonded nonwoven backing with a basis weight of 20 $g/m^2$.

Another layer may be provided on the side of the absorbent body facing the wearer's body, acting as the transfer layer and transfers the fluid to the absorbent body in a suitable manner. This transfer layer is preferably punched or cut out in the same way as the minimum of one part of the absorbent body facing the wearer's body. This transfer layer especially preferably has an open structure which is especially permeable for fluids and has large pores but a low density. For example, laminates of spunbonded nonwoven and carded nonwovens are suitable, with the fluffy side facing up. Such a transfer layer may also have a laminating function (dry and clean).

The transfer layer and/or the minimum of one layer of the absorbent body facing the wearer's body can be differentiated visually from the rest of the sanitary napkin, for example by using a different color for the transfer layer and/or the minimum of one layer of the absorbent body facing the wearer's body than for the rest of the absorbent article.

The transfer layer and/or the minimum of one layer of the absorbent body facing the wearer's body are preferably punched or cut out and applied to one or more other absorbent layer(s) of the absorbent body, preferably made of coform, and preferably bonded together by one of the possible methods mentioned above.

Although the transfer layer and/or the upper layer of the minimum of one layer of the absorbent body facing the wearer's body may have a laminating function, this laminating function may also be assumed, instead or in addition, by the cover layer. The cover layer may in this case contain approximately 1% to 6% titanium dioxide pigment and may have a clean and attractive appearance.

In another preferred embodiment of this invention, the liquid-permeable cover layer may also have a plurality of openings which are formed in it. The size of these openings should be such that a fluid can pass through the cover layer and thereby enter the absorbent body. The openings may be arranged in a longitudinal direction or may be localized in larger numbers in a certain area, which is assumed to be the area that will come in contact with the fluid. The openings should increase the rate at which the body fluids can reach the absorbent body. This facilitates providing a much drier surface for the cover layer than if the openings were not present.

The part of the absorbent body facing the wearer's body may preferably have embossed lines through which the fluid is guided along especially preferred pathways. These embossed lines may also be provided in the transfer layer and/or individual or all of the other layers of the absorbent body.

The cover layer may also be treated with a surfactant to make it more hydrophilic and thus support the absorption of fluid. The surfactant may contain topical additives or internally added materials such as polysiloxanes.

Furthermore, the absorbent article may have another layer on the side of the absorbent body facing away from the wearer's body to act as a distributing layer. In a preferred embodiment, this distributing layer is folded. It may serve as the primary reservoir. It advantageously contains especially small pores and thus has the greatest capillarity in the system of the preferred absorbent article according to the present invention. A melt-blown fiber layer is especially preferably used for the distributing layer. This melt-blown layer of polypropylene, for example, may have a basis weight of 65 $g/m^2$ and in a preferred embodiment it is folded to a final width of 45 mm and a length of 125 mm.

Some or all of the individual layers of the absorbent article may be bonded together in some areas or in totality. In a preferred embodiment, their bonding can be accomplished by using a hot-melt adhesive. Other bonding methods known in the related art, however, should also be included within the scope of the present patent application.

In another preferred embodiment of this invention, the absorbent article according to the present invention has wings on its longitudinal side edges, where the minimum of one layer of the absorbent body facing away from the wearer's body may continue into these wings but need not necessarily extend into these wings. The wings and the longitudinal body of the absorbent article may be provided with a longitudinal adhesive system consisting of a hot-melt adhesive, for example, with a preferred area of 50×190 mm for the longitudinal body of the absorbent article and a preferred area of 20×50 mm for the respective wing adhesive systems of the absorbent article. The longitudinal adhesive system and the wing adhesive systems are each preferably covered by silicone paper or some other possible covering which is known in the state of the art.

The absorbent article according to the present invention is preferably used as a sanitary napkin or as an incontinence diaper.

Furthermore, the absorbent body according to the present invention may include a flow layer and a reservoir layer in a manner familiar to those skilled in the art. Suitable flow layers are made, for example, of cellulose, cellulose-synthetic fiber blends such as coform materials, airlaid-cellulose-synthetic fiber blends, foam materials or high-loft nonwovens and they may contain superabsorbers as an additional component.

Suitable reservoir layers are characterized, for example, by the materials mentioned above for the absorbent body. In an especially preferred embodiment, the minimum of one layer of the absorbent body facing the wearer's body acts as a flow layer.

The absorbent article according to the present invention especially preferably has a density and/or pore gradient. The layer next to the body has the lowest density and the layer next to the liquid-impermeable backing layer has the greatest density. This facilitates diversion of fluid away from the wearer's body.

Such a density and/or pore gradient can be produced in a manner known to those skilled in the art, e.g., by using materials of different densities or by using different pore sizes, etc.

In another aspect, the present invention provides a method of producing an absorbent body, in particular a segmented absorbent body. These absorbent bodies are used in particular in the absorbent articles according to this invention.

A first method according to this invention includes the following steps: a first web of material is brought over a first rotating conveyor element; the first web of material is processed for separation by a second rotating conveyor element along a closed line, creating a first closed dividing seam through the entire thickness of the first web of material; the part of the first web of material outside the first dividing seam is conveyed away over the first rotating conveyor element; the minimum of one part of the first web of material bordered by the first dividing seam is conveyed further with the second rotating conveyor element; a second web of material is conveyed over a third rotating conveyor element; the minimum of one part of the first web of material bordered by the first dividing seam is deposited on the second web of material, and the second web of material is processed for separation by the second rotating conveyor element along the peripheral shape of the minimum of one part of the first web of material bordered by the first dividing seam, thereby creating a minimum of one second self-contained dividing seam through at least partial areas of the thickness of the second web of material, and the minimum of one first and second self-contained dividing seam essentially coincide.

The first web of material and the second web of material may comprise individual materials or multiple materials.

The first web of material and the second web of material may each be composed of one or more layers which may preferably be bonded together with adhesive and which may consist of different materials. The first web of material may comprise in particular layers of the materials used in the minimum of one layer of the absorbent body facing the wearer's body as well as the transfer layer of the absorbent article according to this invention.

The second web of material may comprise in particular layers of the materials used in the minimum of one layer of the absorbent body facing away from the wearer's body and the distributing layer of the absorbent article according to this invention.

The term "self-contained dividing seam" as used in the present invention is understood to refer to dividing seams which define an internal closed geometric shape in a web of material.

The minimum first and second self-contained dividing seams may assume any suitable geometric shape, but the especially preferred shapes are an oval, a triangle, a circle, a tongue or an hourglass. The shape of the layer of the absorbent body facing the wearer's body in the finished absorbent article according to this invention is determined by the shape of the first dividing seam.

In an especially preferred embodiment of the method according to this invention, the second web of material and the minimum of one part deposited on the former and bordered by the first dividing seam is separated into individual units in another step, with each unit comprising a part of the first web of material bordered by the first dividing seam and a frame grid formed by the second web of material.

The term "frame grid" as used here, by analogy with the articles according to this invention described here, is understood to be the part of the material of the absorbent material which remains outside the second dividing seam. The frame grid thus corresponds, for example, to the part of the layer of the absorbent article according to this invention facing away from the wearer's body outside the second dividing seam. The frame grid includes the area of the second web of material defined by the second dividing seam.

In another preferred embodiment of the two methods according to this invention as described here, the individual steps of the method are repeated continuously.

In an especially preferred embodiment of the method according to the present invention, the first web of material is conveyed at a rate corresponding to the peripheral speed of the second conveyor element. This embodiment of the method can be used in particular with the absorbent articles produced according to this invention, when the difference in length between the part of the web of material bordered by the first line, corresponding to the layer of the absorbent body facing the wearer's body and the frame grid formed by the second web of material or the layer of the absorbent body facing away from the wearer's body is not very great, e.g., amounting to less than 25%.

One embodiment of the method according to this invention in which the first web of material is conveyed intermittently and the second rotating conveyor element rotates continuously is especially preferred.

This has the advantage that the cost of materials can be minimized. Due to the intermittent conveyance of the first web of material over the first rotating conveyor element with a second conveyor element rotating continuously at the same time, the first self-contained dividing seams can be worked into the first web of material in a closer sequence in successive separation processing steps than if the first and second conveyor elements were running continuously in synchronization. Therefore, the amount of the first web of material used for the absorbent article can be increased, and the amount of the first web of material discarded and thus the amount of waste can be minimized.

This process management is especially preferred if the difference in length between the layer facing the wearer's body and the layer facing away from the wearer's body is relatively great in the absorbent article produced, e.g., greater than 25%. In these cases, due to the more effective utilization of the first web of material, the method can be less expensive. Intermittent conveyance is understood here to refer to both conveyance at two different successive speeds and interrupted conveyance in phases.

In a most especially preferred embodiment of the method according to this invention, the first and second rotating conveyor elements run in synchronization during the separation working of the first web of material. This has the advantage that the shape of the minimum of one part of the first web of material bordered by the first dividing seam corresponds exactly to the shape of the second dividing seam in the second web of material, when the same dividing elements are used for the two separation processing steps.

In another especially preferred embodiment of the method according to this invention, the rotating conveyor elements are designed in the form of rolls or wheels. These designs permit an especially simple and inexpensive embodiment of this method.

In another especially preferred embodiment of the method according to this invention, the first web of material is processed for separation by means of at least one separating element mounted on the second rotating conveyor element.

It is also especially preferred for the second web of material to be processed for separation by means of at least one separating element mounted on the second rotating conveyor element.

This makes it possible to mount similar separating elements on the second rotating conveyor element, which is especially economical.

The separating element may be, for example, all known cutting or punching devices with which those skilled in the art are familiar. They may be mounted on the second conveyor element in a fixed mount or so they can be telescoped outward.

Due to the fact that the minimum of one part of the first web of material bordered by the first dividing seam is deposited on the second web of material by means of the second conveyor element, this yields a composite web of material in which a particular structure is preformed. In subsequent separation of the composite web of material into separate individual units, these units each include a top layer and a bottom layer, with the top layer having a smaller surface area than the bottom layer, and the bottom layer having a dividing seam corresponding to the shape of the top layer.

In another especially preferred embodiment of the method according to this invention, in another step, the second web of material and the minimum of one part of the first web of material, bordered by the first dividing seam and deposited on the second web, are divided into individual units, with each unit comprising a part of the first web of material bordered by the first dividing seam plus a frame grid formed by the second web of material.

In an especially preferred embodiment of the method according to this invention, an adhesive layer is applied at least to partial areas of the second web of material in order to bond the second web of material adhesively to at least parts of the first web of material. It is especially preferable to provide an adhesive layer only on those areas of the second web of material where the minimum of one part of the first web of material bordered by the first dividing seam has been deposited.

In an especially preferred embodiment of the method according to this invention, a reduced pressure is created in an area of the second conveyor element to support the conveyance of the minimum of one part of the first web of material bordered by the first dividing seam on the second conveyor element.

It is advantageous here to design the second conveyor element as a hollow wheel or roller, where the conveyor element designed to be hollow is preferably subdivided into angular segments by at least one inner bulkhead, and these angular segments may be acted upon by pressure independently of one another in the form of a reduced pressure reservoir, a balanced pressure reservoir or an excess pressure reservoir. The segment of the conveyor element with which the web of material is conveyed is preferably acted upon by reduced pressure.

As an alternative, however, other methods known to those skilled in the art may also be used to support or accomplish the adhesion of the web of material to the second conveyor element and, thus, conveyance of the web of material.

In addition, in another especially preferred embodiment of the method according to this invention, deposition of the part of the first web of material bordered by the first dividing seam onto the second web of material can be accomplished or supported by an excess pressure produced in the area of the second conveyor element.

Deposition of the part of the first web of material bordered by the first dividing seam on the second web of material is supported or accomplished by applying an excess pressure to a suitable angular segment of the conveyor element.

As an alternative, deposition of the part of the first web of material bordered by the first dividing seam onto the second web of material can be supported or accomplished by an elastic ejector.

In another especially preferred embodiment of the method according to this invention described here, several first and second self-contained dividing seams are worked side-by-side into the first and/or second webs of material in spaced apart relationship. This has the advantage that wider webs of material can be used and thus, higher piece numbers of the absorbent articles can be produced per unit of time.

Although the minimum of one first dividing seam always extends throughout the entire thickness of the first web of material, and thus the forms described above are separated from the first web of material, the second dividing seam can extend throughout the entire thickness of the second web of material, or only through partial areas of the thickness of the second web of material. Thus, in the latter case, an intended breaking line is created in the material of the second web of material.

In the absorbent article produced by the method according to this invention, the shape of the layer of the absorbent body facing the wearer's body is determined by the minimum of one first dividing seam.

BRIEF DESCRIPTION OF THE DRAWINGS

The present invention will now be described in detail with the help of the accompanying figures, where:

FIGS. 10 *a* through *k* are especially preferred shapes and punched patterns of the layer of the absorbent body facing the wearer's body.

Figure 1:
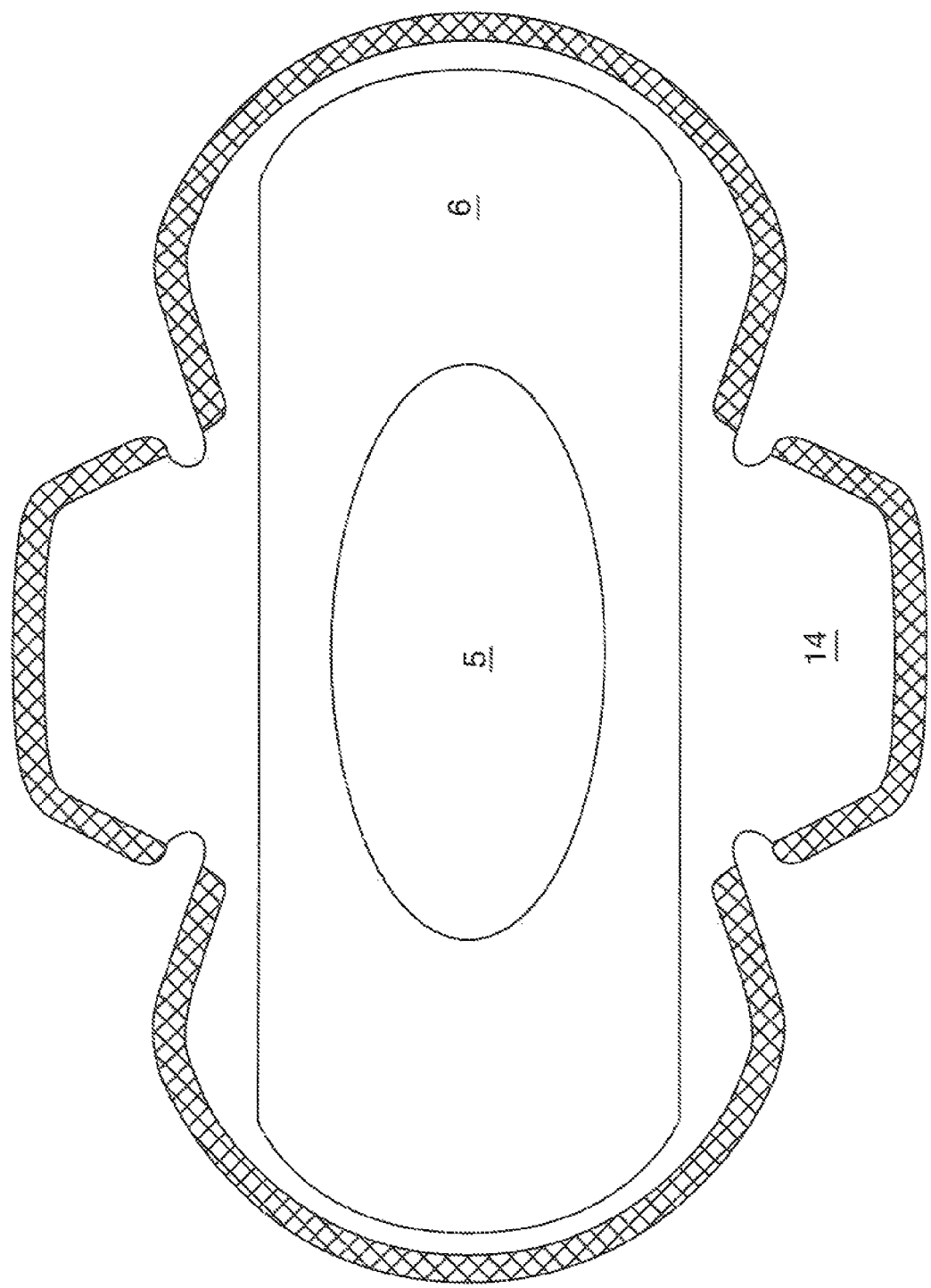
FIG. 1 is a top view of a preferred embodiment of the present invention.

The reference numbers used in the figures have the following meanings:
1: outer cover layer
2: hot-melt adhesive
3: central cover layer
4: transfer layer
5: layer of the absorbent body facing the wearer's body
6: layer of the absorbent body facing away from the wearer's body
7: distributing layer
8: backing layer
9: wing adhesive system
10: covering of the wing adhesive system
11: longitudinal body adhesive system
12: covering of the longitudinal body adhesive system
13: welded seam
14: wing
15: dividing seam
20: first conveyor element
21: second conveyor element
22: separating element
24: third conveyor element
25: first web of material
26: second web of material
28: first self-contained dividing seam
29: second self-contained dividing seam
30: part of the web of material bordered by the first dividing seam
31: part of the first web of material outside the first dividing seam
33: loop forming roller
35: loop forming roller
36: tension rollers
37: tension rollers
38: d.c. motor
39: reduced pressure area
40: screen
41: excess pressure area
42: adhesive device
43: adhesive layer
45: width adjusting roller
46: draw-off roller
47: web width
48: composite web
50: absorbent body

DETAILED DESCRIPTION

Figure 2:
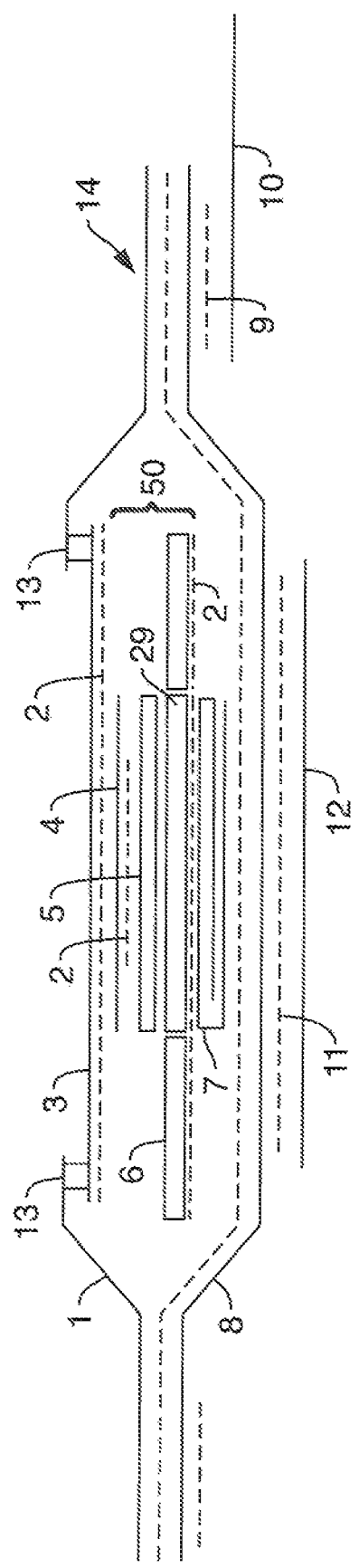
FIG. 2 is cross section through a preferred embodiment of the present invention.
Figure 3:
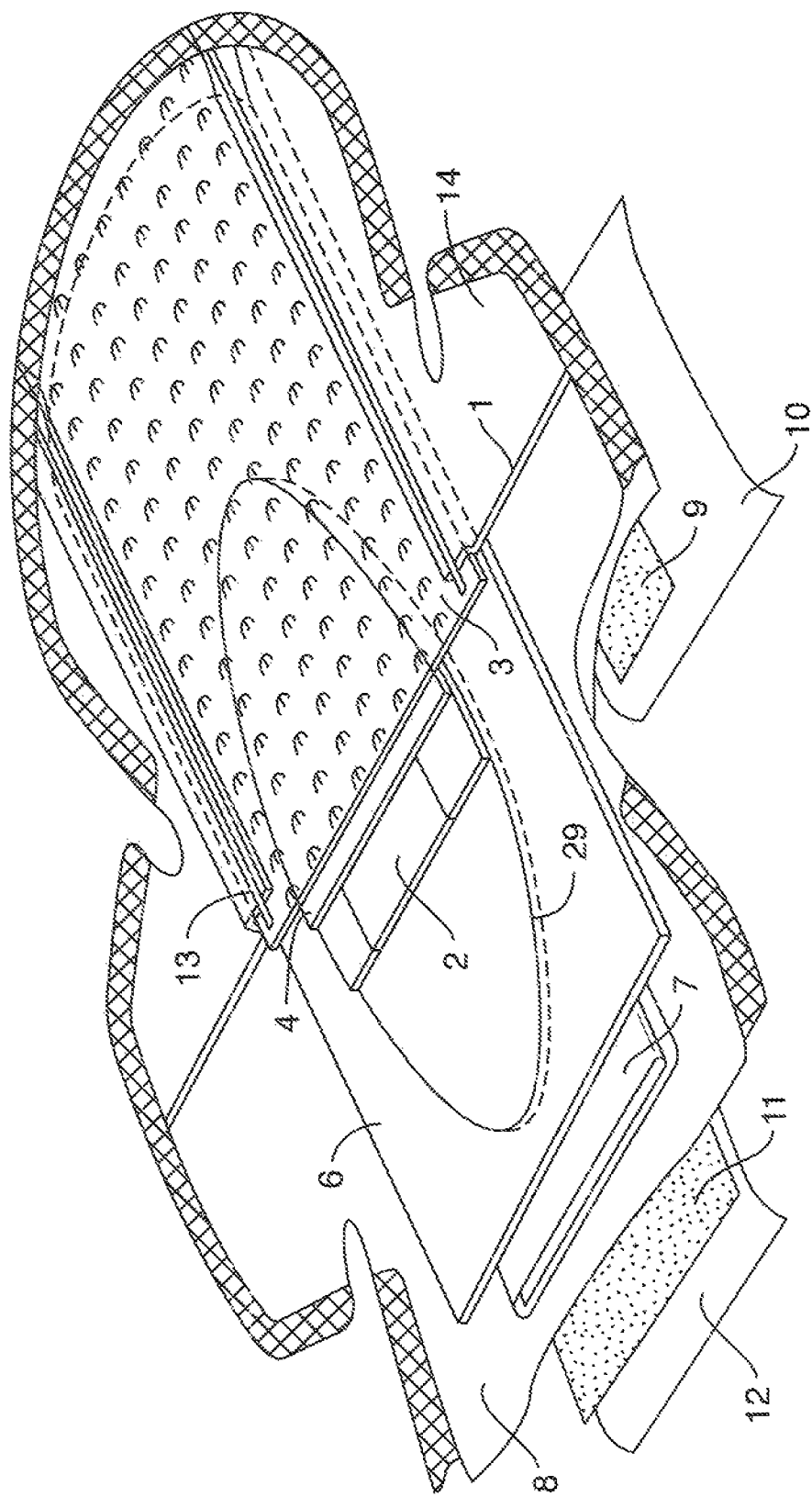
FIG. 3 is a perspective view of a preferred embodiment of the present invention in a partially cutaway view.

The sanitary napkin illustrated in FIGS. 1 and 2 has essentially an hourglass shape with wings 14 that project outwards being formed in the middle of the longitudinal sides and which are tapered toward the middle. The length of the sanitary napkin may be 238 mm, for example, and the width including the two wings 14 is 150 mm, for example. The top layer of the sanitary napkin is formed by an outer cover layer 1 and a central cover layer 3. The central cover layer 3 extends along a central strip over the entire length of the sanitary napkin. The width of the central cover layer 3 may be 70 mm, for example. The central cover layer is made of a perforated polypropylene spunbonded nonwoven with a basis weight of 20 $g/m^2$.

The outer cover layer 1 overlaps with the central cover layer 3 and is bonded to it in the overlap area. This bonding can be accomplished by a welded seam, for example. As an alternative, the two cover layers 1 and 3 may also be bonded together by a hot-melt adhesive. The outer cover layer is also made of a perforated polypropylene spunbonded nonwoven with a basis weight of 20 $g/m^2$ The multi-layer absorbent body of the sanitary napkin is located beneath the central cover layer. In the advantageous embodiment of this invention described here, the absorbent body includes as the top layer the transfer layer 4. The layer of the absorbent body 5 facing the wearer's body is beneath the transfer layer 4 and may also be referred to as an absorbent core. The layer of the absorbent body 6 facing away from the wearer's body is also arranged beneath the layer 5 with the distributing layer 7 arranged beneath it.

The transfer layer 4 is bonded to the central cover layer 3 over its upper surface by means of a hot-melt adhesive 2. The transfer layer 4 consists of a laminate of a spunbonded nonwoven and a carded nonwoven with a basis weight of 52 $g/m^2$ and is arranged in such a manner that the fluffy side of the laminate faces upward, i.e., in the direction of the wearer's body. In addition, the transfer layer is differentiated in color from the remainder of the sanitary napkin.

The layer of the absorbent body 5 facing the wearer's body is arranged beneath the transfer layer 4. The transfer layer 4 and the layer of the absorbent body 5 facing the wearer's body are bonded together by means of a hot-melt adhesive 2. The transfer layer 4 and the layer of the absorbent body 5 facing the wearer's body are punched out in the form of an oval in the present advantageous embodiment of this invention, and they are arranged in the central area of the sanitary napkin. The oval shape has a length of 110 mm, for example, and a width of 45 mm. The layer of the absorbent body 5 facing the wearer's body is made of a coform material, for example, containing cellulose and polypropylene in a weight ratio of 70:30 and having a basis weight of 150 g/m$^2$. It is used together with a spun-bonded nonwoven carrier of polypropylene with a basis weight of 17 g/m$^2$. The laminate of coform material and spunbonded nonwoven carrier has a line embossing with compressed areas.

Especially preferred shapes of layer 5 facing the wearer's body which may be used as an alternative to the oval shape are illustrated in FIGS. 10a-k. In addition, the layers 5 of the absorbent body facing the wearer's body, as shown in FIGS. 10a-k, have internal dividing seams 15 which further segment the layers 5. These dividing seams also may be provided in the same way in layers 4, 6, 7 of the absorbent body above and/or beneath that.

The layer of the absorbent body 6 facing away from the wearer's body is arranged beneath the layer of the absorbent body 5 facing the wearer's body. The layer of the absorbent body 6 extends essentially over the same area as the central cover layer 3, but is shorter in the area of the rounded transverse ends of the sanitary napkin, so that the central cover layer 3 projects over the layer of the absorbent body 6 facing away from the wearer's body in this area. The layer of the absorbent body 6 facing away from the wearer's body may be 220 mm long and 70 mm wide, for example, and made of a coform material of cellulose and polypropylene in a weight ratio of 60:40 and with a basis weight of 90 g/m$^2$. It is used together with a spunbonded nonwoven carrier of polypropylene with a basis weight of 20 g/m$^2$.

An oval punched area provided in the central area of the layer of the absorbent body 6 facing away from the wearer's body corresponds in size and shape to the layer of the absorbent body 5 facing the wearer's body and to the transfer layer 4. Due to the punched area, the layer of the absorbent body 6 facing away from the wearer's body is divided into an inner area and an outer area. The outer area represents the frame grid. The inner oval area of the layer of the absorbent body 6 facing away from the wearer's body lies with complete coverage beneath the layer of the absorbent body 5 facing the wearer's body. The top surface of the layer of the absorbent body 6 facing away from the wearer's body is bonded to the central cover layer 3 by means of a hot-melt adhesive 2 in the area not covered by the layer of the absorbent body 5 facing the wearer's body.

In the central area of the sanitary napkin, the distributing layer 7 is arranged beneath the layer of the absorbent body 6 facing away from the wearer's body. The distributing layer 7 is made of a web of embossed melt-blown material of polypropylene with a basis weight of 65 g/m$^2$ folded on itself to yield a final width of 45 mm with a length of 125 mm, for example. A liquid-impermeable backing layer 8 arranged beneath the distributing layer 7 is made of a polyethylene film with a basis weight of 25 g/m$^2$. The liquid-impermeable backing layer prevents the fluid that has penetrated into the sanitary napkin and been retained there from escaping outward from the absorbent layers at the bottom. The backing layer 8 is bonded to the layer of the absorbent body 6 facing away from the wearer's body and to the central cover layer 3 and the outer cover layer 1 by means of a hot-melt adhesive 2.

In the area of the wings 14, wing adhesion systems 9 are provided on the outer surface of the backing layer 8 facing away from the wearer's body; by means of these wing adhesion systems, the wings 14 can be attached to the side of the wearer's underwear facing away from the wearer's body. The adhesive material may be, for example, a hot-melt adhesive. To protect the adhesive surfaces of the wing adhesion systems 9, they are provided with a covering 10 of silicone paper which can be removed from the adhesive elements before using the sanitary napkin. Before use, the two wings 14 and the side areas of the sanitary napkin can be folded onto the central cover layer 3, so that the wing adhesion systems 9 come to lie side by side. The two wing adhesion systems 9 may then be covered with the covering 10 of silicone paper which may have an area of 70 mm×60 mm, for example.

Additional fixation of the sanitary napkin to the wearer's underwear is made possible by the longitudinal body adhesive system 11 which extends over the central area of the outer surface of the backing layer 8 over an area of 50 mm×190 mm. The sanitary napkin can be attached to the inside of the wearer's underwear with the longitudinal body adhesive system 11. The longitudinal body adhesive system 11 may also be formed by a hot-melt adhesive, for example, and is protected by a second covering 12 which is detachably attached to it. The covering 12 of the longitudinal body adhesive system is also made of silicone paper and has an area of 60 mm×200 mm. The covering 12 is removed before using the sanitary napkin, thus exposing the adhesive surface of the longitudinal body adhesive system 11.

Figure 4:
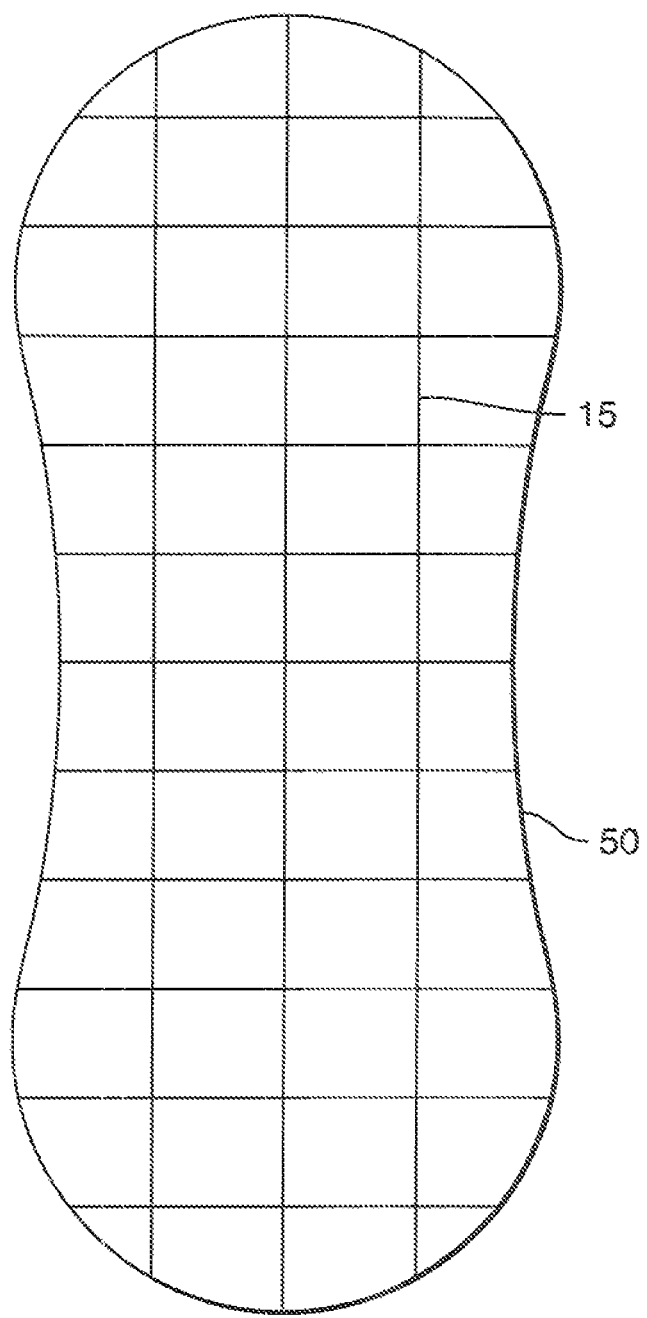
FIGS. 4 through 7 are preferred segmentations in an absorbent body which can be used in preferred embodiments of the present invention.
Figure 5:
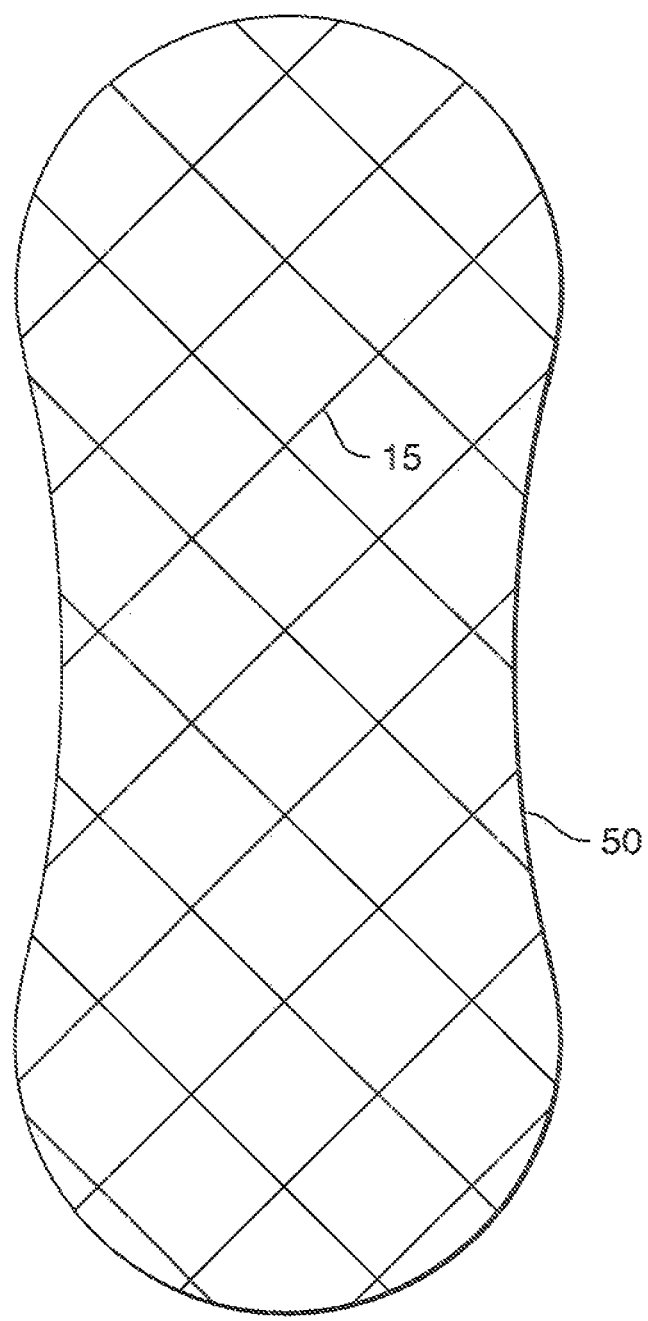
Figure 6:
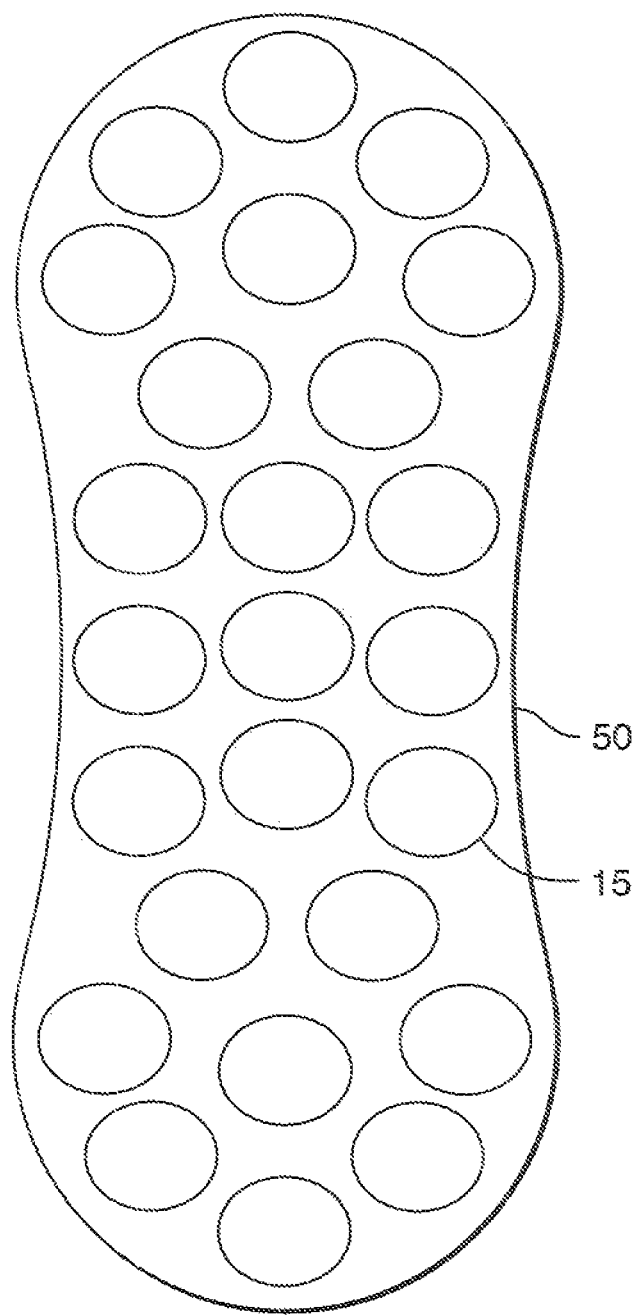

FIGS. 4 through 7 illustrate various segmentation patterns which can be provided in the absorbent body 50 or individual layers of the absorbent body 50 of the absorbent article. FIG. 4 illustrates a square segmentation and FIG. 5 illustrates rhomboidal segmentation. FIG. 6 shows the segmentation in the form of a plurality of circular dividing seams 15.

Figure 7:
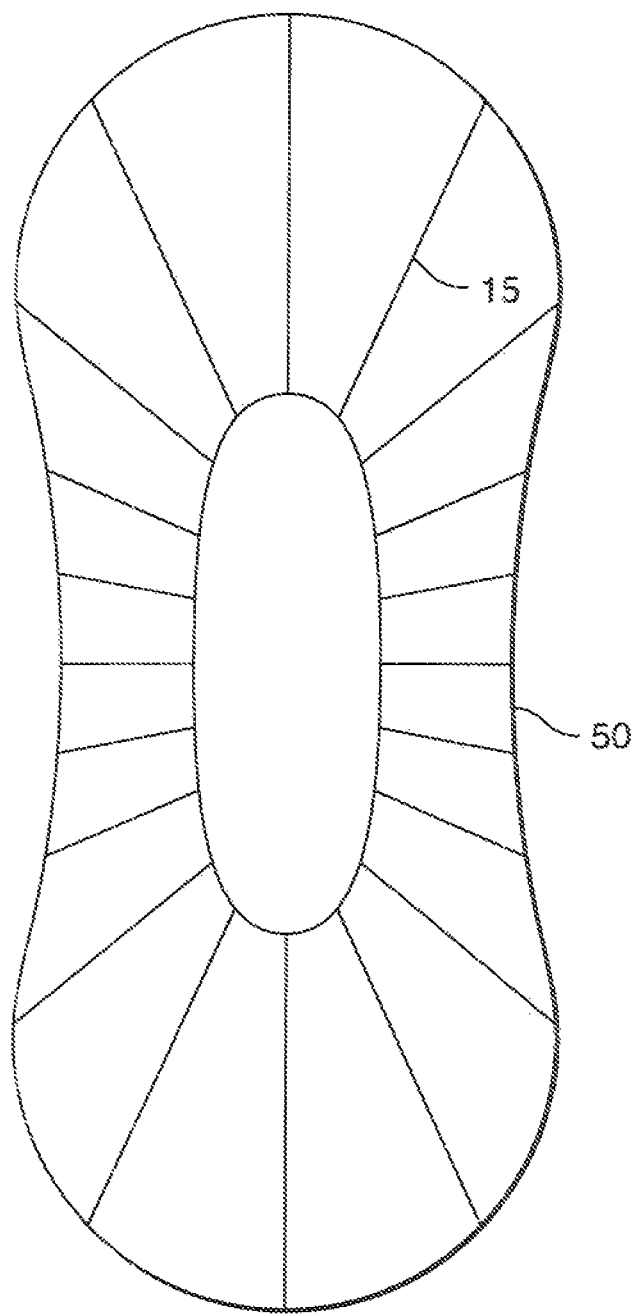

When using an oval-shaped minimum of one layer 5 of the absorbent body facing the wearer's body, the segmentation illustrated in FIG. 7 of at least one of the layers 4, 6, 7 of the absorbent body 50 arranged above and/or beneath it is especially advantageous. Due to the dividing seams 15 extending radially outward from the oval peripheral shape of the minimum of one layer 5 of the absorbent body facing the wearer's body (soleil notching), an especially easy basket shaping of the absorbent article and thus improved suppleness (body fit) to the wearer's body are achieved.

Figure 8:
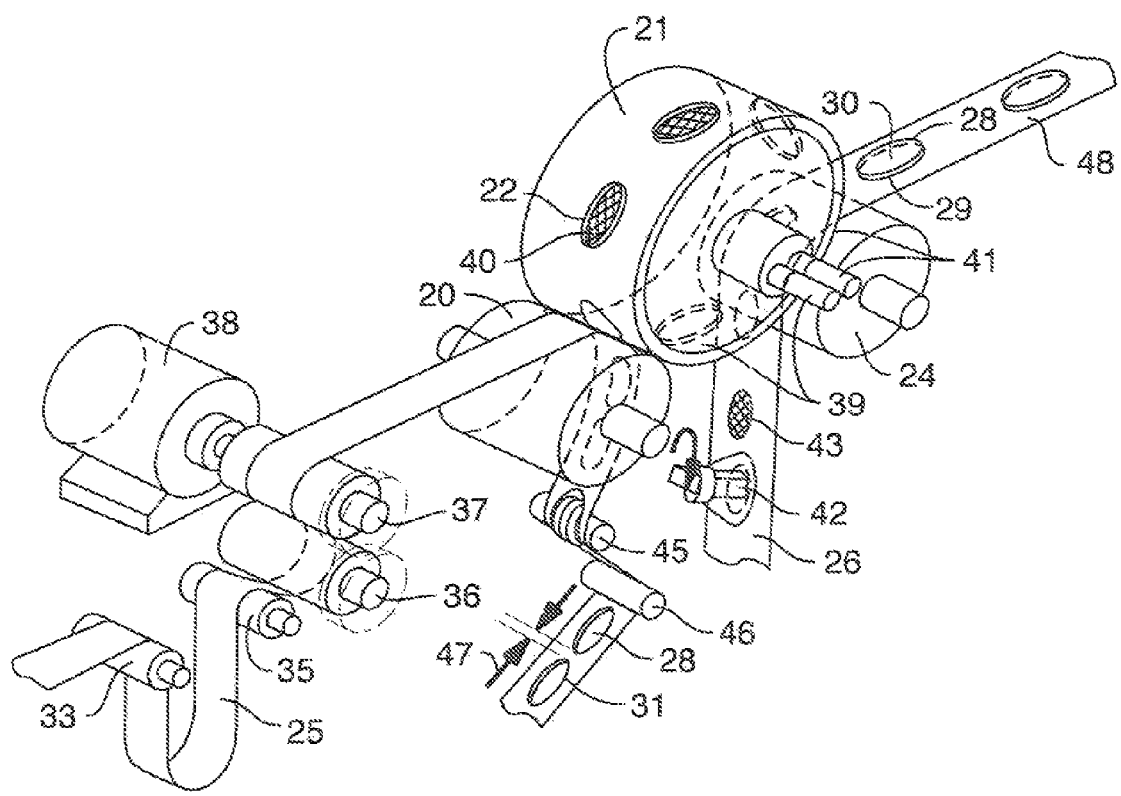
FIG. 8 is a device for carrying out the method of producing an absorbent article.

FIG. 8 illustrates a device for carrying out the method according to this invention.

A first running web of material 25 of absorbent material is conveyed over a conveyor unit (not shown here), e.g., driven conveyor rolls or belts or rollers to two loop-forming rollers 33, 35. A supply loop of the first web of material 25 is formed by the two loop-forming rollers 33, 35. As an alternative, instead of the loop-forming rollers 33, 35, other storage devices with which those skilled in the art are familiar may also be used. The first web of material 25 is then conveyed over two tension rollers 36, 37 that are synchronized but driven intermittently. The first conveyor element 20 is designed here as a counter-cutting roller. The irregular or intermittent drive of the tension rollers 36, 37 is accomplished by an electronically controlled d.c. motor 38, but it may also be provided by other means such as a corresponding hydraulic or mechanical system. For example, it is also conceivable to use cams or disks.

The first web of material 25 is guided between the first conveyor element 20 and a second conveyor element 21 which is designed here as a cutting roller. The cutting roller 21 has a stationary internal bulkhead about which the roller rotates. The bulkhead is configured to separate the interior of the roller (e.g., between the bulkhead and the roller itself) into two areas. The first area, indicated by the reference numeral 39 in FIG. 8 and the reference arrow 39 extending therefrom to the roller 21, is in fluid communication with a vacuum line, which is indicated by the other reference arrow extending from the reference numeral 39 in FIG. 8, so that the first area is always subject to a vacuum as the roller rotates relative to the bulkhead. The second area, indicated by the reference numeral 41 in FIG. 8, is in fluid communication with a positive pressure line, also indicated by the reference numeral 41 in FIG. 8, for receiving pressurized air or gas therein so that the second area is always subject to positive pressure as the roller 21 rotates relative to the bulkhead. Mesh-like screens 40 are applied to the outer shell of the cutting roller 21 at regular intervals along the circumference of the roller. Due to the rotation of the outer shell of the cutting roller 21 either a vacuum pressure or positive pressure can act in the area of each screen 40. Individual separating elements 22 are arranged around each screen 40. These separating elements here are designed as punching devices; as an alternative, however, cutting devices may also be used. Those skilled in the art are familiar with suitable cutting or punching devices. Individual areas 30 of the first web of material are punched out by the punching devices 22 and are conveyed further on the cutting roller 21 by the vacuum pressure acting through the screens 40 in the punched area as the cutting roller rotates past the first area 39 defined by the bulkhead.

The parts 30 of the web of material bordered by the first dividing seam in the method described here are oval. They are referred to below as the absorbent core 30. The part 31 of the first web of material outside the first dividing seam, i.e., the punched grid, is conveyed away after punching over the mating cutting roller 20 and a width adjusting roller 45 and draw-off roller 46. The first web of material 25 is under continuous tension due to the width adjusting roller 45 and the draw-off roller 46.

Due to the intermittent drive of the tension rollers 36, 37, the first web of material 25 reaches a speed corresponding to the peripheral speed of the cutting roller 21 only during the punching operation. Therefore, the distance between two punched-out areas in the punched grid, referred to here as the web width 47, can be kept as small as possible. This is especially advantageous if the absorbent cores 30 are deposited onto the second web of material at a relatively great distance from one another, e.g., if this distance exceeds the length of the absorbent cores 30 by 25%.

A third conveyor element 24 is arranged next to the cutting roller 21 at a distance from the first conveyor element 20 in the direction of production. A second web of material 26, also an absorbent material, is conveyed over an unwinder (not shown) and between the cutting roller 21 and the third conveyor element 24. Due to the punching devices 22 mounted on the cutting roller 21, punched areas (e.g., fold lines) are being worked into the second web of material continuously, having essentially the same shape and size as the punched absorbent cores 30 punched out of the first web of material 25. The absorbent cores 30 are deposited on the second web of material 26 simultaneously with the punching operation. To do so, the cutting roller rotates relative to the bulkhead so that the absorbent core 30 is rotated into fluid communication with the second area 41, which is subject to positive pressure. The positive pressure thus acts on the absorbent core 30 through the corresponding screen 40 during the punching operation to urge the core away from the roller 21 and toward the second web of material. By simultaneously depositing the absorbent cores 30 on the second web of material and punching the second web of material 26, the result is that the second web of material is punched in the resulting composite web 48 along the contours of the absorbent cores 30 deposited on the web.

Adhesion between the absorbent cores 30 and the second web of material is supported by application of adhesive 43 by an adhesive device 42 before punching.

Figure 9:
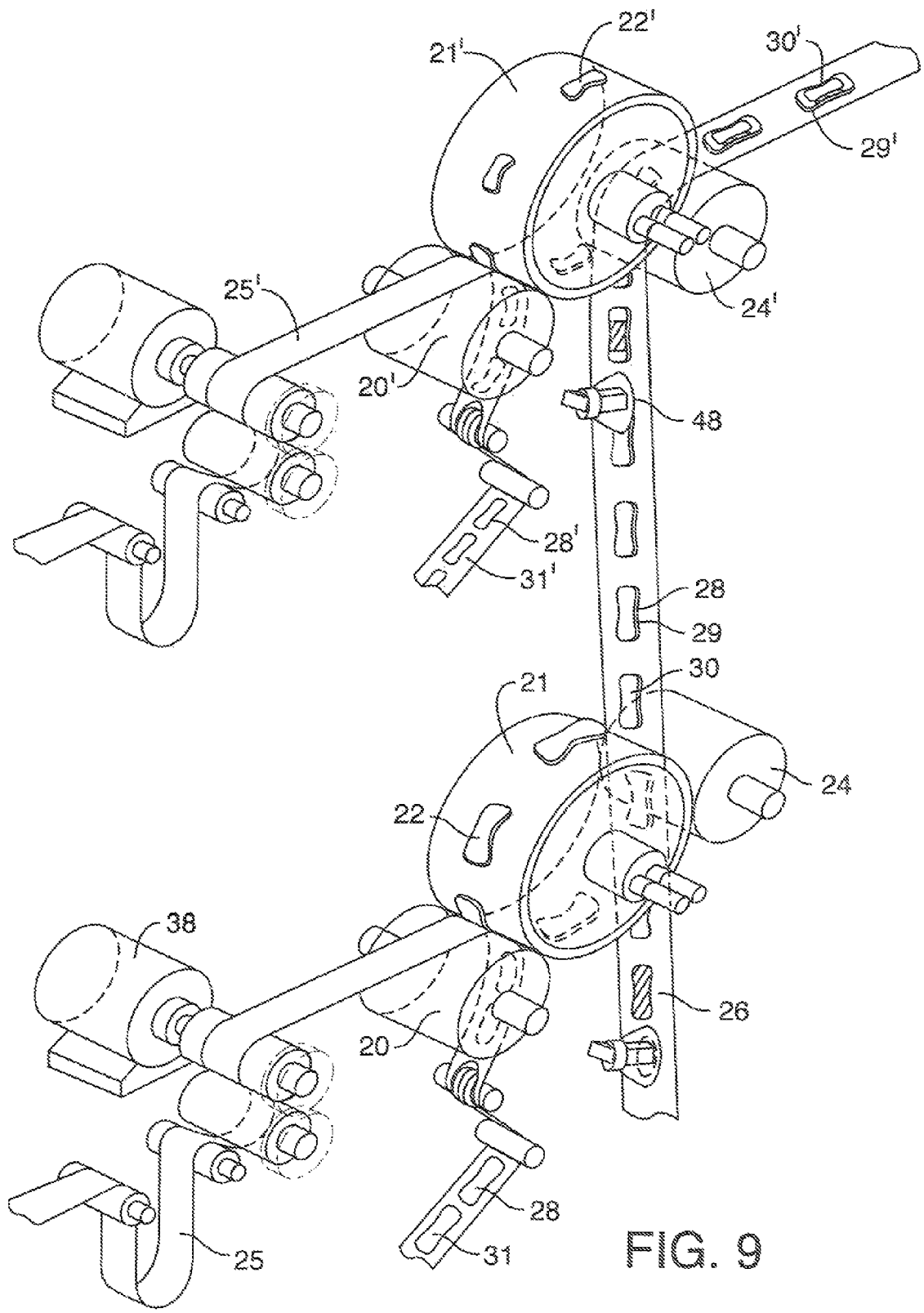
FIG. 9 is another device for carrying out the method of producing an absorbent article.

An intermittent drive of the first web of material is not necessary if the distance between two successive absorbent cores 30 exceeds its own length by less than 25%. The elasticity of the first web of material here makes it possible for the first web of material to be conveyed towards and away at a lower speed than the peripheral speed of the cutting roller 21. Therefore, it is also possible to reduce the amount of the punched grid in the first web of material. FIG. 9 illustrates a method in which two methods as described above are combined in succession. In the method illustrated here, the composite web 48 produced in the first method is used as the second web of material in the successive method.

This makes it possible to deposit additional absorbent cores 30' punched out of a third web of material onto the composite web 48 in corresponding manner and then to segment the composite web 48 through additional punching. The absorbent cores 30' deposited on the composite web 48 in the subsequent procedure may have the same or different shapes and sizes as the absorbent cores 30 punched out of the first web of material and already deposited on the composite web.

What is claimed is:

1. A method of producing an absorbent body for an absorbent article of the type worn by a wearer and having an absorbent body disposed generally centrally of the article and adapted for absorbing liquid body waste released by the wearer, the method comprising the steps of:
    passing a first cut-out from a first web material through a nip;
    passing a second web material through the nip whereby the cut-out from the first web material overlays the second web material as the cut-out and the second web material pass through the nip; and
    performing one of the following as the cut-out from the first web material and the second material together pass through the nip: forming a fold line in the second web material at the peripheral edge of the cut-out of the first web material and forming a second cut-out from the second web material having substantially the same shape as the first cut-out from the first web material.

2. A method as set forth in claim 1, wherein the nip is defined by a pair of conveyor elements, the step of passing the second web material through the nip comprising conveying the second web material over one of the conveyor elements to pass therebetween, at least one of the conveyor elements having one of a fold-line forming device and a cutting device mounted thereon for contacting the second web element at the peripheral edge of the cut-out from the first web-material generally within the nip.

3. A method as set forth in claim 2, wherein the pair of conveyor elements are second and third conveyor elements defining the nip therebetween, the second conveyor element having the one of a fold-line forming device and a cutting device mounted thereon, the method further comprising the steps of conveying a first web material over a first conveyor element to a nip defined by the first conveyor element and the second conveyor element, and contacting the first web of material with the one of a fold-line forming device and a cutting device mounted on the second conveyor element with sufficient pressure to form the first cut-out from the first web material as the first web material passes through the nip formed by the first and second conveyor elements, the step of passing the first cut-out from the first web of material through the nip comprising supporting the first cut-out on the second conveyor element upon rotation of the second conveyor element to convey the first-cut out to the nip formed by the second and third conveyor elements.

4. A method as set forth in claim 3, wherein the first and second conveyor elements are rotating elements from the group consisting of rollers and wheels, the first web of material being conveyed through the nip defined by the first and second conveyor elements at a speed equal to the rotational speed of the second conveyor element.

5. A method as set forth in claim 3, wherein the first and second conveyor elements are rotating elements from the group consisting of rollers and wheels, the first web of material being conveyed through the nip defined by the first and second conveyor elements intermittently while the second rotating conveyor element rotates continuously.

6. A method as set forth in claim 3, wherein the step of supporting the first cut-out on the second conveyor element as the first cut-out is conveyed to the nip formed by the second and third conveyor elements comprises applying a vacuum pressure to the first cut-out to hold the first cut-out on the second conveyor element during rotation of the second conveyor element.

7. A method as set forth in claim 1, further comprising the step of applying adhesive to at least one of the first cut-out from the first web material and the second web material prior to passing the first cut-out and the second web material through the nip such that the first cut-out is secured to the second web material upon passing through the nip.

8. A method as set forth in claim 7, wherein the first cut-out is released from the second conveyor element onto the second web material by subjecting the first cut-out to a positive pressure.

9. A method as set forth in claim 1, wherein the absorbent body has a longitudinal axis and a lateral axis, the fold line formed therein defining at least two segments of the absorbent body, the fold line extending at least in part laterally of the absorbent body, the segments being generally foldable relative to each other along the fold line to facilitate conformance of the absorbent article to the wearer's body.

10. A method as set forth in claim 1, wherein the absorbent body has an inner surface adapted for facing the wearer's body when the absorbent article is worn by the wearer, an outer surface adapted for facing away from the wearer's body, and a thickness, the fold line having a depth that is less than the thickness of the absorbent article.

11. A method as set forth in claim 10, further comprising forming the fold line in at least one of the inner surface and the outer surface of the absorbent body.

12. A method as set forth in claim 10, further comprising forming the fold line within the absorbent body intermediate the inner surface and the outer surface thereof.

13. A method as set forth in claim 1, wherein the absorbent body has a thickness, the fold line having a depth extending substantially through the entire thickness of the absorbent body.

14. A method as set forth in claim 1, further comprising constructing the absorbent body of at least two layers, and further comprising forming the fold line in one of the layers.

15. A method as set forth in claim 14, wherein one of the at least two layers include a flow layer and a reservoir layer.

16. A method as set forth in claim 14, wherein at least one layer of the absorbent body is adapted to be differentiated visually from the remaining layers thereof.

17. A method as set forth in claim 1, wherein the absorbent body has a plurality of fold lines formed therein that define more than two segments of the absorbent body, the plurality of fold lines including the fold line extending at least in part laterally of the absorbent body, the segments being generally foldable relative to each other along the fold lines to facilitate conformance of the absorbent article to the wearer's body.

18. A method as set forth in claim 17, wherein the fold lines are arranged such that the shape of at least one of the segments formed by the fold lines is from the group consisting of a square, a polygonal, and a circle.

19. A method as set forth in claim 1 in combination with the absorbent article, the absorbent article comprising a cover layer adapted for contiguity with the wearer's skin, at least a portion of the cover layer being liquid permeable, and a backing layer in opposed relation with the cover layer, the absorbent body being disposed between the cover layer and the backing layer.

20. A method as set forth in claim 19, further comprising constructing the absorbent body of at least two layers including a transfer layer adjacent the cover layer of the absorbent article and a distributing layer adjacent the backing layer of the article.

* * * * *